United States Patent [19]
Bullinger et al.

[11] 4,330,933
[45] May 25, 1982

[54] FABRICATION METHOD FOR INSTRUMENT MATERIAL HOLDER

[75] Inventors: Henry W. Bullinger, Wilton; Clifford L. Friesel, Redding, both of Conn.

[73] Assignee: The Perkin-Elmer Corporation, Norwalk, Conn.

[21] Appl. No.: 172,589

[22] Filed: Jul. 28, 1980

[51] Int. Cl.³ .............................................. H01C 7/02
[52] U.S. Cl. ..................................... 29/612; 29/407; 29/467; 29/525; 73/15 B; 228/173 A; 228/173 C
[58] Field of Search ................. 29/612, 407, 447, 467, 29/525; 73/15 B, 190 H, 190 CV; 228/170, 171, 172, 173 A, 173 C

[56] References Cited
U.S. PATENT DOCUMENTS 3,524,340 12/1966 Kocherzhinsky .................. 73/15 B
3,732,722 5/1973 Norem et al. ...................... 73/15 B Primary Examiner—Leon Gilden
Attorney, Agent, or Firm—S. A. Giarratana; F. L. Masselle; E. T. Grimes

[57] ABSTRACT

A material holder is fabricated by press-fitting and welding a series of discs into an open cylinder housing. Shrinkage of the cylinder from the welding of the first disc is accommodated by selecting a smaller disc for the second press-fit. A support post is welded to the last disc and shrinkage of that disc from welding of the support post is accommodated by selecting an oversize disc for attachment to the support post. Shrinkage of the last disc also compensates for additional shrinkage of the cylinder from welding of the second disc.

11 Claims, 6 Drawing Figures

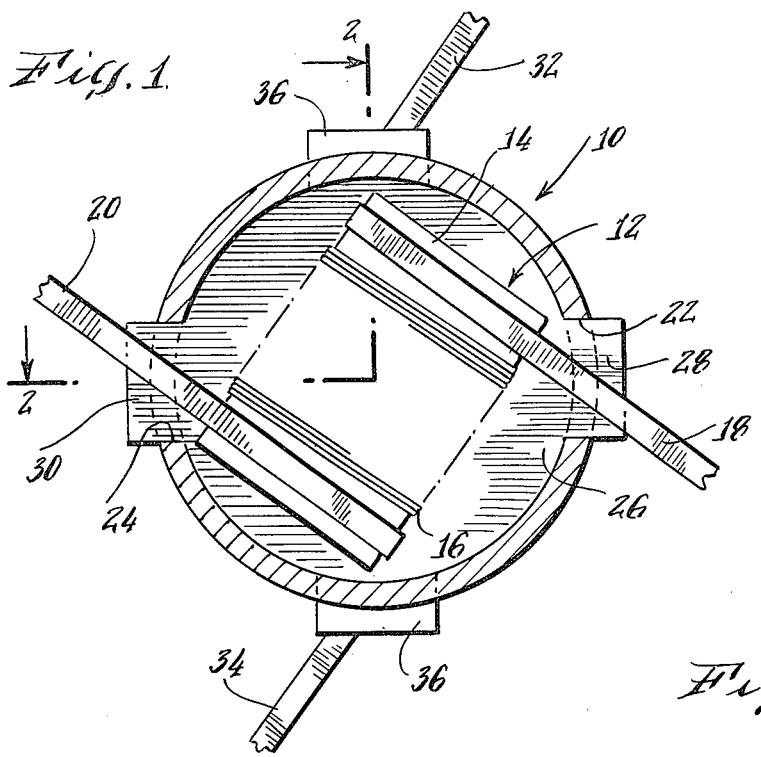
Fig. 1.
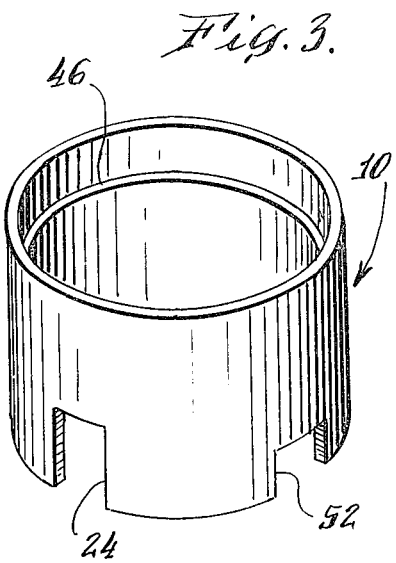
Fig. 3.
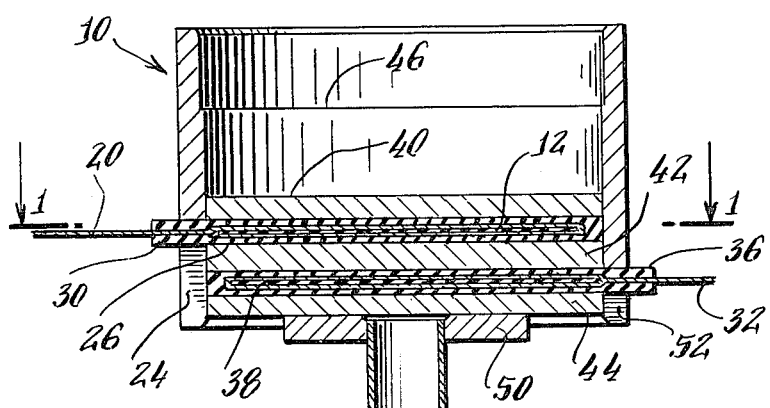
Fig. 2.
Fig. 4.
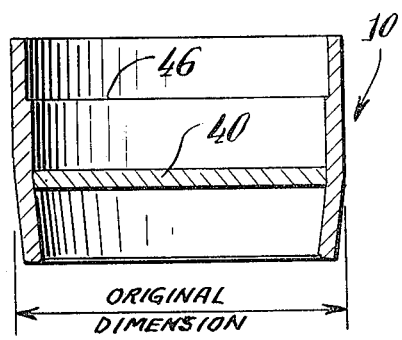
Fig. 5.
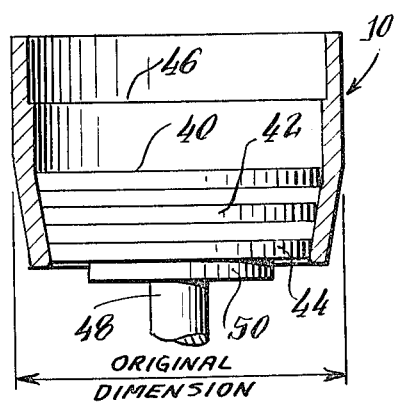
Fig. 6.

FABRICATION METHOD FOR INSTRUMENT MATERIAL HOLDER

BACKGROUND OF THE INVENTION

The present invention relates to an improved fabrication method for holders for materials used in measuring instruments such as calorimeters, and it is particularly useful in a differential scanning calorimeter.

The present invention particularly relates to a material holder used in a differential scanning calorimeter of the type disclosed and claimed in U.S. Pat. No. 3,732,722 for a "MATERIAL HOLDER" issued May 15, 1973 and invented by Norem et al and assigned to the Perkin Elmer Corporation of Norwalk, Conn. A differential scanning calorimeter is a thermal analytical instrument which operates on the principle that thermal energy is absorbed or evolved during physical or chemical changes in a material which is being analyzed. The differential scanning calorimeter measures the differential energy changes that occur in a sample material as compared to a reference material, during such physical or chemical changes. The sample material and a thermally inert reference material are placed in separate material holders in the same thermal environment and their temperatures are measured during the analysis process.

The material holder, as disclosed in the aforementioned patent, consists of a cylindrical cup having three bottom partitions forming two cavities within the bottom portion of the cup, one of the cavities containing a heating winding, and the other cavity containing a heat-sensing winding. A supporting center post is attached to the bottom of the lowermost partition as a support for the material holder.

In order to produce the material holder, a series of substantially identical discs are punched from sheet stock with a punch and die set to form the three partitions. These discs are successively press fitted into a cylindrical housing and electron beam welded at the disc edges to the cylindrical housing. The heater and sensing windings are sandwiched between the successive disc partitions.

Serious problems have been encountered in the above-described assembly and fabrication method in that it has been found to be extremely difficult to maintain tolerances on the disc diameters and the inside diameters of the cylindrical housings with sufficient precision to avoid very high rejection rates in the assembled material cups. The success of the instrument resides in maintaining extreme precision. The precision in measurement is so important that a noble metal such as platinum, paladium, gold, and their alloys are preferably used as the material of the material holder. Preferably, the metal of which the holder is formed is an alloy of 80% platinum and 20% iridium. The noble metals avoid the problems of oxide formation.

The high precision also requires extremely narrow tolerances in the assembled dimensions of the material holders. Thus, in a material holder which is in the order of one-third of an inch in diameter (actually 0.360 inches in one preferred embodiment), the various partitions must be perfectly parallel with one another with a variation out of parallelism not to exceed 0.001 inch. Also, the various partitions must not be distorted in shape, the compartments containing the windings must be absolutely consistent and uniform in size, within the tolerance of plus or minus seven ten thousandths of an inch, and there must be very good conductivity between the edges of the partition discs and the cylindrical housing. In order to accomplish these purposes, the partitions must be press fitted into position within the cylindrical housing with a tight enough fit to precisely maintain the position of each disc during handling after assembly and before electron beam winding. Furthermore, the press fit must be sufficiently tight to promote the production of a good sound electron beam weld between the disc partition and the cylindrical housing in order to provide a consistently high thermal conductivity through the joint formed thereby. On the other hand, the disc must not be press fitted with so much of an interference fit that it results in distortion of the disc.

One of the biggest problems in achieving the satisfactory press fit of the disc partitions into the cylindrical housing apparently arises because of variations in the diameters of the discs produced by the punch and die set. For a particular batch run of approximately 900 discs between sharpenings of the punch and die set, it has been discovered that the disc diameters may vary in a typical range of about 3/10,000ths of an inch, or more. These variations in disc diameter are believed to be associated with the wear pattern of the punch and die, and also, possibly, these variations may be related to variations in the toughness and thickness of the sheet metal from which the discs are punched.

Accordingly, it is one object of the present invention to provide an improved fabrication method which avoids the problems arising from variations in the disc diameters as produced by the punch and die.

Another problem in providing the correct press fit arises particularly in connection with the bottommost disc partition to which the support post is welded. It has been discovered that the support post welding causes the disc to which it is welded to shrink somewhat in diameter, that shrinkage being in the order of 4 to 5 ten thousandths of an inch.

Accordingly, it is another object of the invention to provide an improved fabrication method which avoids the problem associated with the shrinkage in the diameter of the bottommst disc partition occasioned by the welding of the support post thereto.

Another major problem in producing a satisfactory press fit of the disc partitions has been found to result from the fact that the electron beam welding of the first (uppermost) partition into the cylindrical housing causes the diameter of that housing to shrink slightly, so as to increase the tightness of the cylinder around the edges of subsequently assembled disc partitions. Similarly, the electron beam welding of the second disc partition causes still a further shrinking of the cylindrical housing for the assembly of the third disc partition.

Accordingly, it is another object of the present invention to provide an improved fabrication method which avoids the consequences of the problem of the shrinkage of the cylindrical housing resulting from the electron beam welding of earlier assembled disc partitions in order to improve the press fit of subsequently assembled disc partitions.

Further objects and advantages of the invention will appear from the following description and the accompanying drawings.

SUMMARY OF THE INVENTION

In carrying out the invention in one preferred form thereof, an improved fabricating method is employed which compensates for at least part of the fluctuations in disc diameters, and which compensates for the shrinkage of the cylindrical housing during electron beam welding of the first disc which includes the steps of sorting the discs according to diameter into at least two sets including a first set and another set having diameters smaller than the discs of the first set. Cylindrical housings are then machined with an inside diameter somewhat smaller than the outside diameters of the discs of the first set to provide a press fit of the discs of the first set within the housings. After press fitting and electron beam welding of a disc from the first set within each cylinder housing, one of the discs from the smaller diameter set is press fitted into the housing, the smaller diameter of the disc compensating for the shrinkage of the cylinder caused by the welding of the first disc.

In another aspect of the invention, an improved fabrication method may be provided in which the discs are divided into at least two sets, including a first set and another set of discs which are larger in diameter than the discs of the first set. A batch of cylindrical housings are then machined with an inside diameter to provide a desired press fit of the discs of the first set within the housings. After a disc from the first set is press fitted into a cylindrical housing and welded therein, one of the larger diameter discs, to which a supporting center post has already been welded, is press fitted into the end of the cylindrical housing. The reduction in the diameter of the last mentioned disc caused by the welding of the center post compensates for the larger initial diameter of the disc and the reduction in the diameter of the cylindrical housing caused by the welding of the earlier disc into the housing.

The above mentioned fabrication processes are preferably combined into a single process in which the initial run of discs is sorted by diameter into a first set, another set of discs having a diameter smaller than the discs of the first set, and still another set of discs having a diameter larger than the discs of the first set, the discs of the first set being used as the first disc partition to be positioned and welded into each cylindrical housing, the inside diameter of which has been machined to provide the appropriate press fit, the smaller diameter discs being used as the second partition to be press fitted and welded into each housing, and the larger diameter discs being the ones to which supporting posts are attached prior to press fitting and welding into the cylindrical housing to provide the third partition. The first set of discs is sometimes referred to hereinafter as the set of "medium" or "intermediate" size, the smaller diameter set is sometimes referred to as the smallest, and the larger diameter set is sometimes referred to as the largest.

BRIEF DESCRIPTION OF THE DRAWINGS

FIG. 1 is an enlarged sectional top view, taken at section 1—1 in FIG. 2, of a calorimeter instrument material holder assembly to which the present invention relates and illustrating how one of the windings and associated insulators fit into the housing.

FIG. 2 is an enlarged sectional side view of the assembly of FIG. 1 taken at section 2—2 of FIG. 1.

FIG. 3 is a perspective view of a cylindrical housing portion of the assembly of FIGS. 1 and 2.

FIG. 4 is a perspective view of a partition disc which is to be press fitted into the cylinder of FIG. 3 in the assembly of FIGS. 1 and 2.

FIG. 5 is a sectional side view, corresponding to FIG. 2 and showing a partial assembly and illustrating, in an exaggerated way, how the cylindrical housing shrinks after the first disc partition is welded into place.

FIG. 6 is a sectional side view corresponding to FIG. 2 and showing substantially the full assembly, as in FIG. 2, but illustrating in an exaggerated way, how the cylindrical housing shrinks, and how the smaller diameters of the second and third partitions compensate for that shrinkage.

DESCRIPTION OF THE PREFERRED EMBODIMENTS

Referring more particularly to FIG. 1 of the drawings, there is shown a sectional top view of a material holder which is produced in accordance with the present invention and illustrating a winding assembly 12 which is intended to be housed within a cavity within the material holder between adjacent disc partitions. The material holder is preferably constructed in accordance with the teachings of U.S. Pat. No. 3,732,722, previously mentioned above. The material holder includes a cylindrical housing 10 and the winding assembly 12, which includes a winding holder 14 which preferably consists of a solid aluminum oxide chip upon which a platinum wire winding 16 is wound. A pair of platinum ribbons 18 and 20 are soldered to the ends of the winding 16 and serve as lead-out connectors. The lead-out connector ribbons 18 and 20 emerge through oppositely arranged slots 22 and 24 in the sides of the cylindrical housing 10. The winding assembly 12 is insulated from the adjacent disc partition of the assembly by means of an insulator disc 26, which includes tabs indicated at 28 and 30 extending through the slots 22 and 24 to insulate the lead-out connectors 18 and 20. Another insulating disc (not shown) of identical construction is assembled on top of the winding assembly 12 to insulate that assembly from the next metallic disc partition. The insulating layers, such as 26, may be formed of alumina cloth to withstand high temperatures.

A second winding is provided at a level below the winding assembly 12, and is provided with similar lead-out connectors 32 and 34, and insulators, as illustrated at 36.

FIG. 2 is a side sectional view of the assembly of FIG. 1. The second winding is illustrated at 38. In FIG. 2, the three disc partitions are shown at 40, 42, and 44.

On the inside surface of the housing 10, in the upper portion thereof, there is a larger diameter portion terminating in a shoulder indicated at 46 which is arranged to receive and support a cover, not shown. The material to be tested is supported upon the uppermost disc partition 40, sometimes referred to hereinafter as the first disc partition.

Attached to the bottom of the lowermost partition 44, there is a center post 48. Center post 48 is attached to the disc 44 by means of a washer member 50. The center post 48 is first electron beam welded to the washer 50, and the washer 50 is electron beam welded to the disc partition 44. The disc partition 44 is then press fitted into the cylindrical housing 10 and then later electron beam welded at its outer edges to the housing 10.

In the fabrication of these material holders, the assembly essentially takes place from bottom up. Thus, the first (upper) partition disc 40 is first press fitted into the cylindrical housing 10, and electron beam welded into place. Next, the upper insulator for winding 12 is inserted, the winding 12 is inserted, and the lower insulator is inserted. The slots such as slots 22 and 24, shown in FIG. 1 and FIG. 2 extend all the way through the bottom edge of the housing 10 so that the insulator tabs 28 and 30, and the winding lead-out ribbons 18 and 20 are easily and conveniently accommodated during this assembly step. Next, the intermediate partition 42 is press fitted into the cylindrical housing, to the position shown in FIG. 2, and electron beam welded into place. The insulators 36 associated with winding 38, and winding 38, are then assembled in proper order. A pair of slots for the lead-out ribbons of winding 38 are similarly provided in the lower portion of the cylindrical housing 10, as indicated at 52 and extending all the way to the bottom to permit ease of assembly of winding 38. Finally, the bottom partition 44, to which the center post 48 and the center post washer 50 have already been attached, is press fitted into the position shown in FIG. 2, and electron welded into place.

When properly assembled and welded, the partition discs 40, 42, and 44 are thermally united with the metal of the housing 10 so that there is a very efficient transfer of heat from one to the other, as required in the operation of the calorimeter.

FIG. 3 is a perspective view of the cylindrical housing 10 of the embodiment of FIGS. 1 and 2 prior to assembly of the other parts. FIG. 3 thus shows the edge slots 24 and 52 with greater clarity.

FIG. 4 is a perspective view of one of the disc partitions 40 prior to insertion into the cylindrical housing 10.

Despite the exercise of extreme care in fabrication of the material holders, maintenance of close dimensional tolerances upon component parts, and selective testing of the finished product and matching of pairs of material holders having similar characteristics for use in individual calorimeters, it has been found that there has been a very high and unacceptable rate of spoilage and rejection in the production of the material holders.

Most of these rejections appear to arise primarily because of improper press fits of the partition discs 40, 42, and 44 within the cylindrical housing 10.

One improper press fit is too loose a fit, which will not maintain the partition in the proper position long enough for the mechanical handling between the press fit operation and the welding operation. Also, a press fit which is too loose does not provide for a good electron beam weld. One of the chief disadvantages of a poor weld is that the thermal conductivity through the weld is deficient. The free transfer of heat through the welded joints is essential for proper measurements by the calorimeter. The other improper fit is too tight a fit, resulting in an unacceptable mechanical distortion of either the partition or the housing.

Despite efforts to hold close tolerances in the manufacture of the partition discs 40, 42, and 44, and in the cylindrical housing 10, it has been found to be very difficult to obtain exactly the right amount of interference press fit of the discs into the housing 10. The difficulty appears to arise from three major causes as follows:

1. The diameters of the discs, as punched out by the punch and die, typically vary over a range of at least three ten thousandths of an inch for a production run of 900 discs between sharpenings of the punch and die. It is believed that this variation in disc diameter may arise from various factors including die wear, and slight variations in the thickness and toughness of the sheet material from which the partitions are punched.

2. Shrinkage of the inside diameter portions of the cylindrical housing which are to accommodate subsequent partition discs caused by welding of the first and second partition discs to be assembled. This has been discovered to be an important factor also. The shrinkage which is encountered is shown in an exaggerated form in FIG. 5. FIG. 5 particularly illustrates how the bottom end of the cylindrical housing 10 shrinks in diameter due to welding of the first disc partition 40. For clarity, the original dimension of the outer diameter is indicated in FIG. 5. It will be understood that the inner diameter is likewise reduced by the prior weld. It is not known just why this shrinkage should occur, but it has been observed that it does occur. The shrinkage of the housing at the position to which the second disc partition 42 is press fitted due to the welding of the first disc partition 40 has been found to be from about one to two ten thousandths of an inch. Furthermore, the shrinkage of the housing diameter at the position to which the third disc partition 44 is press fitted due to the welding of the first and second disc partitions 40 and 42 has been found to be from about two to four ten thousandths of an inch.

3. The third cause of the problem is the shrinkage of the bottom disc 44 which has been observed to occur because of the welding of the center post 48 and the center post washer 50 to the bottom disc. This shrinkage in the outside diameter of the bottom disc 44 has been found to be from about three to about five ten thousandths of an inch.

Since it has been discovered that an interference or press fit, in order to be satisfactory, must be in the range from at least one ten thousandths of an inch to no more than four ten thousandths of an inch, the above diameter variations are seen to be very important in producing a satisfactory product. In the above statement, an interference or press fit of one to four ten thousandths of an inch is used in the conventional sense that the outside diameter of a disc partition must exceed the associated inside diameter of the cylindrical housing by no less than one ten thousandths and no more than four ten thousandths of an inch.

In accordance with the present invention, a fabrication method is followed which ingeniously takes advantage of the various fluctuations in disc diameters and the fluctuations in cylinder diameters to accommodate the disc partitions to the cylindrical housings to provide a very high yield of material holders which conform to the desired specifications for accuracy and weld quality.

For instance, in accordance with one aspect of the invention, a batch of discs are produced by punching the discs from sheet metal with a punch and die, and the discs are sorted according to diameter into at least two sets of discs including a first set consisting of discs having the smallest diameters and a second set consisting of discs having medium diameters. A batch of cylindrical housings is then machined with an inside diameter of each cylindrical housing being machined to be within the range of one to three ten thousandths smaller than the average outside diameter of the medium diameter discs. One of the medium diameter discs is then press fitted into each cylindrical housing 10 and electron beam welded into place to form the top partition 40 of the material holder. The winding 12 and the associated insulators which are to occupy the upper cavity are then assembled against the bottom of the upper disc partition, and one of the discs from the set of smallest diameter discs is then press fitted into each cylindrical housing and electron beam welded into place to form the second disc partition 42. The smaller diameter of the smallest diameter set of discs compensates for the shrinkage of the inside diameter of the cylindrical housing 10 due to the electron beam welding of the first disc partition 40.

In accordance with another aspect of the invention, as the discs are punched they are sorted according to size into a set consisting of the largest diameter discs, as well as a set of discs having medium diameters. Again, the cylinder is machined on its inside surface to provide a press fit of from one to three ten thousandths for the medium diameter discs to form the upper partition 40. The largest diameter discs are then used for the bottom disc 44. The center post 48 and the associated center post washer 50 are electron beam welded to the individual largest diameter discs 44. This welding causes shrinkage in the outside diameter of the disc 44 and it is then press fitted into the cylindrical to form the bottommost disc partition. The shrinkage of the outside diameter of disc 44 caused by the welding of the center post 48 and center post washer 50 accommodates for the shrinkage of the inside diameter of the cylinder 10 due to the electron beam welding of the prior disc partitions. The shrinkage of the outside diameter of disc 44 due to the center post welding also compensates for the large beginning size of the outside diameter of the disc.

Preferably, all of the principles recited above are combined in one fabrication process in which the discs are sorted into three sets consisting of small, medium and large discs respectively. The housings are then machined to provide a one to four ten thousandths of an inch press fit with the medium diameter discs. The medium diameter discs are then used for the upper partition 40, the small diameter discs are used for the intermediate partition 42, and the large diameter discs, after shrinkage by welding of the center post, are used for the bottom disc partition 44.

FIG. 6 substantially repeats the basic structure illustrated in FIG. 2, but in simplified form, and shows in exaggerated form (as in FIG. 5) the shrinkage of the cylinder 10 in response to the welding of the first and second discs 40 and 42, and the reduced diameters of the second and third discs 42 and 44 in the completed assembly which compensate for that shrinkage. These features, plus the machining of the inside of cylinder 10 to initially provide a precise press fit for the first disc 40 constitute a triple diametric compensation.

In order to minimize inspection costs, the diameters of the discs are preferably measured only by measuring samples as the discs are produced to provide an approximate measurement for all of the discs in the groups of discs sampled. For instance, when a batch of 900 discs is produced, a sample disc diameter may be measured at the beginning of the run, and after the production of each batch of 100 discs. The batch beginning and ending measurements thus provide an indication of the average diameter of the discs in each group of 100. The groups of 100 discs may then be sorted, according to size, to form the three sets of discs, the smallest, the medium, and the largest.

In one preferred embodiment of the invention, the inside diameter of the material holder is about one third of an inch, and the thickness of the cylindrical wall of the cylindrical housing is about 20 thousandths of an inch. The thickness of the disc partitions is also about 20 thousandths of an inch.

While this invention has been shown and described in connection with particular preferred embodiments, various alterations and modifications will occur to those skilled in the art. Accordingly, the following claims are intended to define the valid scope of this invention over the prior art, and to cover all changes and modifications falling within the true spirit and valid scope of this invention.

We claim:

1. An improved method of fabricating a circular material holder for a measuring instrument such as a differential calorimeter;

the method comprising the steps of forming a batch of the discs sufficient for production of a batch of predetermined size of the material holders by punching the discs from sheet metal with a punch and die, sorting the discs according to diameter into at least two sets of discs including a first set and another set consisting of discs having diameters smaller than the discs of said first set, the number of discs in each set being substantially equal, machining a batch of cylindrical housings with the inside diameter of each cylindrical housing being machined to be somewhat smaller than the outside diameters of the first set of said discs to provide a press fit of said first set of discs within said housings, press fitting one of said discs from the first disc set into each housing and electron beam welding the disc into place to form the top partition of the material holder, assembling a coil and associated insulators against the bottom of the partition formed by the welded disc and press fitting into each housing one of the discs from the set of smaller diameter discs to form a second partition within said housing and electron welding the second partition disc into place.

2. An improved method of fabricating a circular material holder for a measuring instrument such as a differential calorimeter;

the method comprising the steps of forming a batch of the discs sufficient for production of a batch of predetermined size of the material holders by punching the discs from sheet metal with a punch and die, sorting the discs according to diameter into at least two sets of discs including a first set and another set consisting of discs having diameters larger than the discs of said first set, the number of discs in each set being substantially equal, machining a batch of cylindrical housings with the inside diameter of each cylindrical housing being machined to be somewhat smaller than the outside diameters of the first set of said discs to provide a press fit of said first set of discs within said housings, press fitting one of said discs from the first disc set into each cylinder and electron beam welding the disc into place within the cylinder to form the top partition of the material holder, assembling a coil and associated insulators against the bottom of the partition formed by the welded disc, welding a supporting center post to one side of each disc in the set of larger diameter discs, and press fitting one of the discs carrying the welded center post into the bottom end of said housing and electron beam welding that disc in place to form a second partition.

3. An improved method of fabricating a circular material holder for a measuring instrument such as a differential calorimeter which includes a metal cylindrical housing initially open at both ends and into which a plurality of substantially identical metal discs are press fitted and welded to form a cup having at least one internal compartment;

the method comprising the steps of forming a batch of the discs sufficient for production of a batch of predetermined size of the material holders by punching the discs from sheet metal with a punch and die, sorting the discs according to diameter into three sets of discs including a first set, a second set consisting of discs having diameters smaller than the discs of the first set, and a third set consisting of discs having diameters larger than the discs of the first set, the number of discs in each set being substantially equal, machining a batch of the cylindrical housings with the inside diameter of each cylindrical housing being machined to be somewhat smaller than the outside diameters of the first set of said discs to provide a press fit of said discs within said housings, press fitting one of said discs from the first disc set into each cylinder and electron beam welding the disc into place within the cylinder to form the top partition of the material holder, assembling a coil and associated insulators against the bottom of the partition formed by the welded disc and press fitting into each housing one of the discs from the set of smaller diameter discs to form a second partition within said housing and electron beam welding the second disc partition into place, welding a supporting center post to one side of each disc in the set of larger diameter discs, assembling a coil and associated insulators against the bottom of the second partition formed by the second disc within said housing, and press fitting one of the discs carrying the welded center post into the bottom end of each housing and electron beam welding that disc in place to form a third partition.

4. A method as claimed in claim 3 wherein the discs are sorted according to diameter by first separating the batch of formed discs into a plurality of successively produced groups each containing substantially equal numbers of discs, measuring the diameters of at least some sample discs from each group in order to provide an indication of the diameter of the discs in each group, and then sorting the groups of discs according to diameter into three sets of groups of discs to provide the first set consisting of the groups of discs having intermediate diameters, a second set consisting of the groups of discs having diameters smaller than the discs of the first set, and a third set consisting of the groups of discs having diameters larger than the discs of the first set.

5. A method as claimed in claim 4 wherein the metal used for fabrication of said material holder is selected from one of the group of precious metals including platinum, paladium, gold, and their alloys.

6. A method as claimed in claim 5 wherein the metal used in fabricating the material holder is a platinum-iridium alloy.

7. A method as claimed in claim 4 wherein the diameter of the material holder is about one-third of an inch and the thickness of the wall of the cylindrical housing is about twenty thousandths of an inch and the machining of the inside diameter of each cylindrical housing is carried out to provide an inside diameter which is between one and three ten thousandths of an inch smaller than the average outside diameter of the medium diameter set of discs to provide for the press fit of the medium diameter discs within the housing prior to welding.

8. A method as claimed in claim 7 wherein the variation in the average outside diameter for different groups of discs within a production batch of discs is about three ten thousandths of an inch.

9. A method as claimed in claim 8 wherein the shrinkage of the inside diameter of the housing at the position where the smaller diameter disc is press fitted into the housing as the second disc partition is in the order of one to two ten thousandths of an inch due to the electron beam welding of the first disc into the housing as the top partition.

10. A method as claimed in claim 8 wherein the shrinkage of the inside diameter of the housing at the position where the bottom disc carrying the welded center post is press fitted into the housing is in the order of three to five ten thousandths due to the prior electron beam welding of the first disc as the upper partition and the smaller diameter disc as the intermediate partition into the housing.

11. A method as claimed in claim 10 wherein the shrinkage of the larger diameter discs caused by the welding of the center posts thereto ranges in the order of three to five ten thousandths of an inch.

* * * * *